United States Patent [19]
Womack et al.

[11] Patent Number: 5,818,592
[45] Date of Patent: Oct. 6, 1998

[54] NON-CONTACT OPTICAL GLIDE TESTER

[75] Inventors: Kenneth Womack, San Diego; L. Allan Butler, Carlsbad; Michael Wahl, San Diego, all of Calif.

[73] Assignee: Phase Metrics, Inc., San Diego, Calif.

[21] Appl. No.: 797,740

[22] Filed: Feb. 7, 1997

[51] Int. Cl.⁶ ................................................ G01B 9/02
[52] U.S. Cl. ...................... 356/357; 356/345; 356/359
[58] Field of Search .............................. 356/345, 357, 356/347, 359, 360

[56] References Cited

U.S. PATENT DOCUMENTS

5,486,924   1/1996   Lacey ............................... 356/357
5,504,571   4/1996   Eckerman et al.

*Primary Examiner*—Robert Kim
*Attorney, Agent, or Firm*—Blakely Sokoloff Taylor & Zafman

[57] ABSTRACT

A non-contact optical method and apparatus for use in inspecting and measuring defects on a disk. The apparatus generates an interference pattern from a reference beam reflected from a surface of a transparent slider with a second beam reflected from a surface of a test disk. The resulting interference pattern is processed by a set of photodetectors and processing electronics to quantify and map the location and magnitude of asperities on the disk.

29 Claims, 5 Drawing Sheets

NON-CONTACT OPTICAL GLIDE TESTER

BACKGROUND OF THE INVENTION

1. Field of the Invention

The present invention relates generally to the field of magnetic disks. More specifically, the invention relates to apparatus and techniques for inspecting the surfaces of a magnetic disks for defects and the like.

2. Background of the Invention

In recent years microcomputer equipment such as personal, desk top or lap top computers have become extremely popular for a wide range of business, educational and recreational uses. Such computers typically include a main central processor having one or more memory storage devices such as magnetic recording disks for the storage of data. The typically rigid storage disk or disks are often part of a so-called Winchester disk drive unit, sometimes referred to as a "hard" disk. In contrast, the flexible disk of a so-called "floppy drive" is more akin to tape recording media, albeit it is rotated rather than a linearly driven strip.

Hard disk systems typically consist of one or more circular, rigid disks mounted on and rotated by a common spindle. Each disk contains a plurality of narrow, closely spaced concentric tracks wherein serial data can be magnetically recorded and later recovered by a transducer or transducers positioned with respect to the desired track. Each transducer is part of a head assembly which is integrated into a slider. The slider is gimbal mounted by a flexure to a spring, which is further attached to a rotary arm. A voice coil motor pivots and moves the slider radially across the surface of a magnetic disk from one data track to another.

During operation of the hard disk, the rotation of the magnetic disk causes the air layer closest to the surface to spin at virtually the same speed as the disk. This generates a flow of air dragged under the slider. It is this air flow which causes the slider to "fly" above the disk surface. This hydrodynamic lifting phenomena from the aerodynamic interaction between the slider and the rotating disk is termed an "air bearing". Actual physical contact is avoided by the lubricating film of air, in spite of the mounting spring force pressing the slider against the disk.

The increasing memory demands of modern computers and software result in a strong need for magnetic recording technology which increases the density at which information can be recorded and read. The total memory storage capacity or recording density is proportional to the number of tracks on the surface of a disk and the linear bit density. The overall recording density is strongly dependent upon the air bearing height. The current trend in the industry is toward increasing storage capacity by reducing the height of the air bearing. In state-of-the-art disk drive units, flying heights have been reduced to be on the order of one microinch above the surface of the disk.

Reducing flying heights to such low levels mandates that the magnetic disks have smooth surfaces free of defects. Any asperities (i.e. localized surface-height peaks) on the disk surface may induce undesirable contact between the head and the disk. The friction of contact generates heat and temperature changes which may change the physical characteristics of the head. Magneto-resistive (MR) heads are particularly sensitive to variations in temperature.

Unfortunately, during the manufacturing process, the magnetic recording surface may be inadvertently damaged resulting in scratches, pits or voids. Alternatively, contaminant particles introduced in the manufacturing process can end up causing imperfections on the disk surface. These imperfections can adversely affect the way the head flies or result in a loss of magnetic data. For example, a rough surface texture with numerous defects projecting above the planar surface of the disk can cause destructive head crashes. Conversely, pits or voids extending below the disk surface in the recording surface may result in a loss of magnetic information.

Because of the aforementioned demands on disk surface characteristics, manufacturers of magnetic recording disks must devote considerable time to certifying the surface characteristics of their magnetic disks. Typically, this involves a visual inspection of the disk surfaces for defects. In more thorough inspections, disk certification testers are used. The disk certification testers typically contain a piezoelectric or acoustic emission transducer mounted to a slider known as a glide head. The piezoelectric transducer is "flown" over the disk at a chosen flying height. Any disk asperities projecting beyond the chosen flying height will strike the piezoelectric transducer and induce a resonance in the transducer. The mechanical energy is converted to an electrical signal by the transducer. The size and number of asperities can be measured by analyzing the electrical signal produced by the piezoelectric transducer in this so-called glide test.

Lower air bearing thicknesses require slide heads that "fly" closer to the surface of the disk. The violent impact between protrusions and a transducer so close to the disk surface increase the likelihood of secondary damage to the disk caused by flying debris and abrasions of subsequent contacts. Other problems with piezoelectric detection of asperities include the difficulty in measuring pits in the disk and the need for detailed information on flying height which typically requires separate tests to measure flying height and asperities. Thus a non-contact technique of measuring small asperities on the disk is needed.

Optical inspection instruments are capable of identifying and characterizing physical defects on a disk. There are, for example, commercial interferometers configured to inspect surfaces for defects and morphology. Imaging interferometers are in principle capable of measuring the shape and size of a disk defect within limits set by the resolving power of the instrument. Such instruments, however tend to be slow, expensive, and difficult to integrate into a disk manufacturing process.

Current art for obtaining height data for surface defects on disks include measuring the calibrated fly height behavior of a certifier slider and its associated piezoelectric sensor, and off-line inspection using a phase shift interference microscope as in products marketed by Wyko, Zygo, and Phase Shift Technology. The speed of inspection of these off-line instruments is unacceptably slow for production testing of 100% of the disk surface.

Thot Technologies currently markets a system for using doppler interferometry to measure surface characteristics of a disk. The doppler system reflects a single beam of light from the surface of a rotating disk and determines the relative changes in surface characteristics by measuring a doppler shift. However, this technique suffers from several drawbacks. Because only one reference beam is used, the dimensions of measured defects is limited by the wavelength of the light used in the measurement. Thus the current implementations of the Doppler system cannot measure defects on the order of one micron. A second drawback of such doppler systems is that because doppler systems measure velocity (a change in surface topology) an integration constant is needed to determine the absolute height of defects. This constant is difficult to determine. Thus there is a need for a system capable of directly measuring distances and having an improved resolution.

Ideally, the certifying process should both qualify and quantify the type, as well as the location, of imperfections present on the surface of the recording medium. To avoid problem areas during recording, there is also a need to map the entire disk surface so as to be able to locate defects and classify them including information on whether the defects are pits or bumps. A process which avoids wear and tear on device components and combines both positive and negative surface excursion measurements with flying height measurements is particularly desirable.

As will be seen, the present invention provides an apparatus and method for optically inspecting the surfaces of magnetic disks. According to the invention, defects and problem areas are pinpointed with an optical detection apparatus capable of measuring and differentiating between various types of defects. The invention also satisfies the need for an inspection tool that provides both qualitative and quantitative analysis of the disk's surface. The inspection apparatus is highly accurate and provides a simple, cost-effective method for certifying magnetic disks. The invention described here provides height data much like the off-line instruments, but due to the massively parallel feature processing its test time is compatible with 100% production tests of disk surfaces.

SUMMARY OF THE INVENTION

The present invention is a non-contact technique of measuring surface defects on a rotating disk. Defects may be pits or peaks—i.e. either negative or positive excursions of the surface from the mean level. The measuring apparatus includes a transparent slider which is flown above the surface of the disk being measured. A light source illuminates the disk through the slider. An interference pattern is created between the beam reflected from the slider and the second beam reflected from the disk surface. An optical receiver detects the light reflected from the slider-disk interface. The interference pattern is detected at frequent points in time, and processed to determine the distances from a surface of the slider to the multiple points on the disk surface which were moving through the measurement field at the time of reflection. The sequence of distances is further processed to identify significant variations from the mean, which are profiled, mapped, and classified as passing or failing compliance with specifications.

DETAILED DESCRIPTION OF THE INVENTION

An optical apparatus and method is described for detecting and measuring surface defects including both pits and peaks or asperities on a rotating disk. In the following numerous specific details are set forth such as particular elements, power levels, distances, etc., in order to provide a thorough understanding of the present invention. However it will obvious to one skilled in the art that the invention may be practiced without these specific details. In other instances, well known techniques, materials, components, etc. have not been shown or described in detail in order to avoid obscuring the invention.

Figure 1:
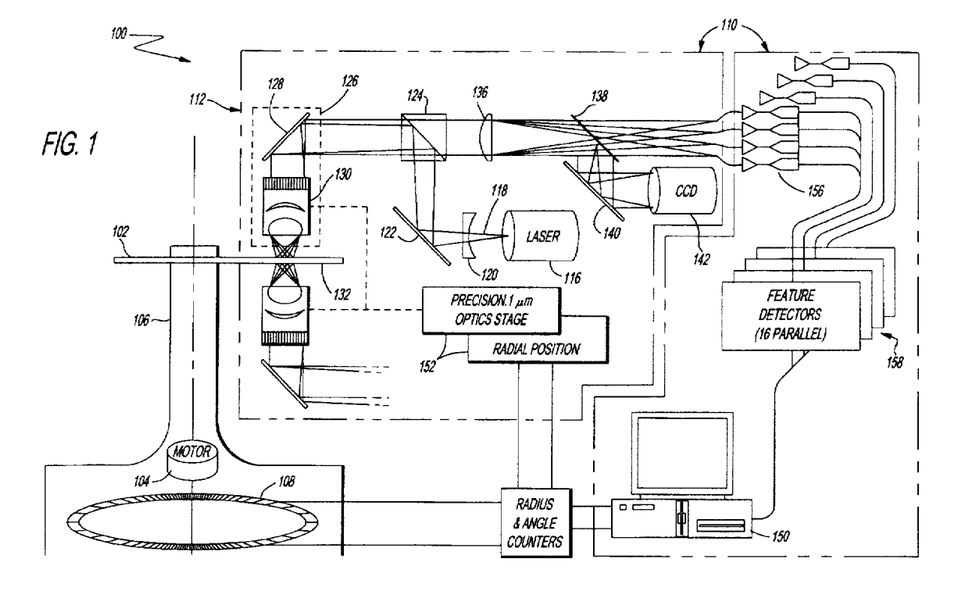
FIG. 1 is an overall schematic of one embodiment of the non-contact optical glide tester.

FIG. 1 shows an overview of the disk inspection system 100. A disk inspection system 100 is designed to measure defects and asperities on a disk 102 being tested without contacting the surface. The disk inspection system includes a drive motor 104 rotating a spindle 106 which in turn spins the disk 102 which is being tested. A set of sensors 108 such as a shaft encoder determines the angular position of the disk 102 and sends that information to appropriate synchronizing electronics.

The disk inspection system 100 comprises an optically-based glide tester system 110 which includes an interferometric system that repetitively determines the relative phase shift between light reflected from a reference surface and multiple points on the disk 102 as the disk rotates. The glide tester 110 includes a top portion which rests above the disk 102 and measures defects on the top surface of the disk. In one embodiment, the top portion of the glide tester 110 is duplicated in a symmetrical bottom portion which measures defects on the bottom side of the test disk 102. To simplify the discussion, only the top portion of the glide tester will be discussed. However, in the preferred embodiment, duplicate optics on the bottom side of the disk under test will be implemented enabling more rapid certification of a double sided disk.

The top portion of the glide tester 110 comprises an interferometer in which a light source 116, such as a 30 milliwatt helium neon laser produces a light beam 118 passing through lens 120 and reflector 122. A beam splitter 124 directs a portion of the beam to an optical head assembly 126. In one embodiment, the beam splitter 124 is a 50:50 beam splitter, thus half of the light from light source 116 arrives at the optical head assembly 126. In the preferred embodiment, the other half of the light may be advantageously used for the duplicate optics.

In accordance with the principles of the present invention, the optical head assembly 126 comprises optical elements which provide optical interference between a reference beam and a sampling or information beam. The reference beam may for example be generated using a transparent flat positioned in close proximity to the surface under test. In this arrangement, interference is generated in accordance with variations in the optical path due to changes in the surface-disk spacing. Alternatively, a reference surface may be provided in a Michelson-type arrangement, where the light beam in the optical head assembly is split into a reference path and a sampling path. In this case, provision for a large optical path difference should be considered. In yet another embodiment of the optical head assembly 126, a Nomarski or other sheared beam arrangement may be used to provide a differential interference signal. In accordance with the principles of the present invention, these and other interferometric imaging arrangements comprising the optical head assembly 126 may be used in conjunction with the preferred image capture apparatus to provide an accurate, high-speed disk inspection system. As will be appreciate by those skilled in the art, an imaging interferometer and rapid, parallel signal processing is advantageously combined to provide optically based disk inspection including optical glide.

A preferred embodiment of the optical head assembly 126 comprises a reflector 128 and an objective lens 130 used for directing light to the disk and a transparent slider (not shown in FIG. 1) above the test disk 102. Light reflected from the proximal surface (i.e. closest to the disk) of the transparent slider interferes with light reflected from the top surface of the disk 102. This light propagates back through the optical head assembly 126, through the beam splitter 124 and long-focus lens 136. A pellicle or glass plate beam splitter 138 reflects a small portion of the light while transmitting most of the intensity. The low-intensity light is steered by reflector 140 to an imaging device, typically a charge coupled device ("CCD") or video camera 142. The video camera image is viewed by an end user to determine whether the system is operating properly, such as ensuring proper positioning of the optical head assembly 126 over the test disk 102. The video camera may also be used for other diagnostic purposes such as visual verification of the cleanliness of the glass slider and approximate visual confirmation of electronic data generated by the glide tester. The reflector 140 is typically a partial reflector only (i.e. a beam splitter). Transmitted light is used for auto-focus detection not shown in FIG. 1.

The major portion of the beam is transmitted through splitter 138 and fed to an optical detector, preferably a detector array 156. The detector array 156 is typically coupled to real-time feature detectors 158. Data rates at the detector inputs are extremely high, typically beyond present PC computer capability in each of the many parallel channels. Thus the desired feature information must be distinguished from the majority of featureless surface data, and only the feature data is forwarded to a computer 150.

Furthermore, the radial positioning of the optical head assembly 126 should be controlled accurately enough to scan the disk without gaps. Preferably the computer 150 orchestrates the initial positioning of the optical head assembly 126 using precision optic stages and drive motors 152 which move the assembly radially to the rim of the disk, sets the initial spindle speed, and positions the head optical assembly 126 close to the spinning disk. Then the computer asserts an enable signal to dedicated control electronics which coordinates the radial position of the head and rotational speed of the disk. Preferably as more of the disk is scanned and the head moves closer to the center of the disk, the rotational speed of the disk increases to maintain a constant linear disk speed under the head. The radius decreases faster and faster such that during one complete revolution the head is closer to the center by exactly one scan width. The resulting spiral scan views the disk at a constant area per second, and since the whole scan is at maximum data rate this is preferred way to scan the whole disk.

For example, in order to complete the scan of a typical disk in approximately 30 seconds or less, a possible disk linear velocity would be $1.25 \times 10^4$ mm/sec. To achieve such linear velocities in a typical 95 mm diameter disk, the disk should rotate at around 2,500 revolutions-per-minute ("RPM") when the head gimbal assembly is at the outer edge of the disk and increase to around 7,500 RPM when the head gimbal assembly reaches about one-third radius.

The optical receiver such as the detector array 156 is preferably a photodiode array composed of a series of individual photodiodes in an array configuration. The outputs of the photodiode array 156 are amplified and sent to a series of feature detectors 158. The feature detectors are typically macro-programmable logic chips such as chips made by Altera. The feature detectors operate in parallel and determine whether a signal indicating a particular defect fulfills certain predetermined criteria. Typically pits shallower than some depth or peaks lower than a set height will be ignored. It is possible to have multiple height criteria to distinguish mild and severe defects. The feature detectors 158 may also be programmed to look for other predetermined patterns or features.

A computer 150 receives the information on identified defect types and the sequence of surface heights representing the defect profile from the feature detectors 158. This information is tagged with the radial and angular location of the feature, and transferred to the processor in the personal computer 150 which processes and records the information. Using the accumulated information, a defect map of the disk 102 may be made. Adjacent tracks having a feature at the same angle may have their defects combined in a mosaic, for example of a scratch extending across multiple tracks of the scan. The defect information may be used to determine whether a disk should be accepted or rejected.

Figure 2:
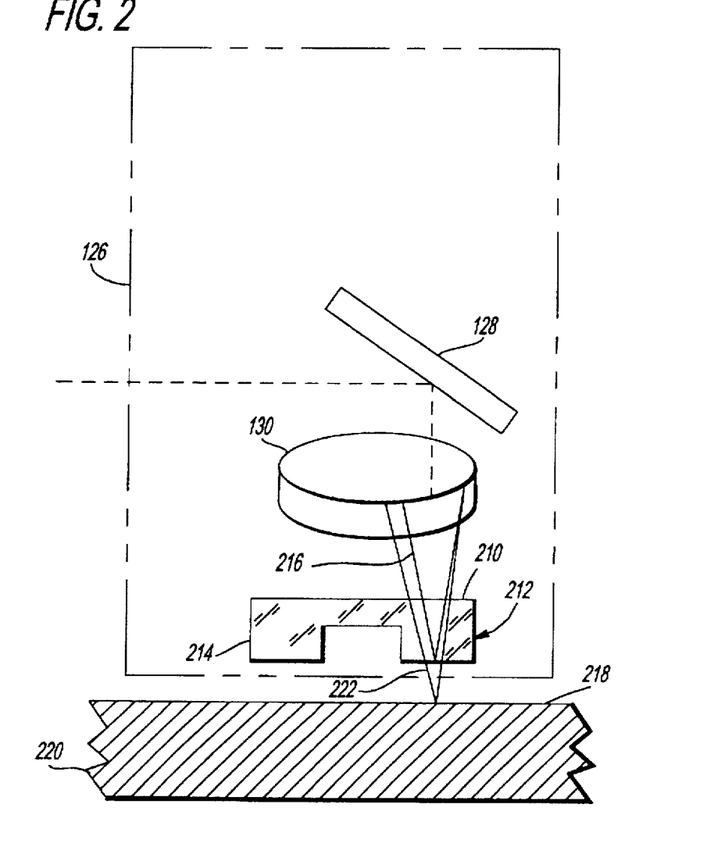
FIG. 2 is an expanded view of the interface between the disk under test and the optical head assembly.

FIG. 2 is an expanded view of a preferred optical head assembly 126. Light reflected from the beam splitter 124 (of FIG. 1) enters the optical head 126 where it is steered by a reflector 128. Reflector 128 directs the beam of light through an objective lens 130. In an alternative embodiment, the lens 130 is a 20× differential interference contrast microscope objective, such as a Nomarski objective, and no glass slider is used. In this case, the detector signal produced by a surface defect is a result of interference between two sheared images rather than interference between a glass slider and the disk.

FIG. 2 further illustrates the optical path through the preferred optical head assembly 126 and the test disk which produces the optical interference pattern. Light from the lens 130 passes through a first surface 210 of a transparent slider 212 and reflects off the proximal surface 214 of slider 212. The reflected beam 216 serves as a reference beam for the interferometer. Some of the light continues past the second surface 214 of the transparent slider 212 and reflects off a surface 218 of the test disk 220. This second information beam 222 is the beam which interferes with the reference beam 216 to allow determination of the distance from the bottom surface of the slider 214 to the top surface 218 of the test disk 220.

One method of measuring the distance between the slider and disk surface is by interferometry wherein, the light that is reflected from two surfaces 214, 218 are combined to form an interference pattern which depends on the spacing between the reflecting surfaces. The analysis of interference fringe patterns has been discussed in a number of references including the article *Inteferometric Measurement of Disk/Slider Spacing: the Effect of Phase Shift on Reflection* by C. Lacey, R. Shelor, A. Cormier and F. E. Talke in the September/October 93 issue of IEEE Transaction on Magnetics.

The measurement of an opaque slider/transparent disk spacing using various types of interferometry, is commonly done to determine slider flying height, e.g. Phase Metrics fly height tester. When using monochromatic light to illuminate the slider/disk interface, the intensity (I) of the light reflected from both surfaces is a function of the light reflected from the disk $r_1$, the light reflected from the slider $r_2$, and the total phase difference between the two waves $\delta$. For normally incident light, the intensity equation for the interference pattern is given by:

$$I = \frac{r_1^2 + r_2^2 + 2r_1 r_2 \cos\delta}{1 + r_1^2 r_2^2 + 2r_1 r_2 \cos\delta} \quad (1)$$

The total phase difference $\delta$ is given by the equation:

$$\delta = \frac{4\pi h}{\lambda} + 2\pi - \phi_d \quad (2)$$

where h is distance from the bottom surface of the slider 214 to the top surface 218 of disk 220. $\lambda$ is the wavelength of the incident light and $\phi$ is the phase shift on reflection. Thus the total phase difference $\delta$ is a function of the phase shift on reflection off the disk surface $\phi$ and the phase difference caused by the difference in path length between the two waves given by the $$\frac{4\pi h}{\lambda}$$

term. The negative sign on $\phi_d$ is the result of the most commonly used sign convention and the $2\pi$ has been added simply to keep $\delta$ positive for all values of h. The $2\pi$ could be eliminated with no effect on equation 1. The round trip path length difference of the beam reflected from the slider is twice the slider/disk spacing h.

Equations 1 and 2 can be used to calculate the distance from the bottom surface of the slider 214 to the top surface of the disk 218 height h because all the other variables ($\lambda$, $r_1$, $r_2$, $\phi_d$ and $\lambda$) are measured or known.

One problem with using the interference measurements is noise which may occur from unwanted reflections. In one embodiment, such noise is minimized by placing an anti-reflection coating on the top surface 210 of slider 212 to avoid reflections coming off of the top surface and interfering with light beams 216 and 222. In another embodiment the slider is wedge shaped or faceted (either longitudinally or transversely) so the top is not parallel to the disk surface and its reflection is not visible to the photo-detectors. Processing electronics compensate for other noise which comes from multiple reflections within the slider 212 between surfaces 214 and 210 and other optical elements in the beam. The processing electronics also compensates for multiple reflections between slider surface 214 and test disk surface 218.

Optical reference beam 216 and information beam 222 reflecting from disk 220 propagate back through the objective lens 130 and reflect off reflector 128 before exiting the optical head assembly 126.

In another embodiment of the present invention, the slider 212 of the optical head assembly 126 may be replaced by a reference surface such as a transparent flat (not shown). The transparent flat is preferably mounted in a fixed position with respect to the focusing optics 130. The focusing lens 130 and transparent flat may then be adjusted together by the autofocus mechanism.

In yet another embodiment of the present invention, the slider 214 focusing optics 130 may be replaced by a Nowarski-type objective. The image projected by the Nowarski objective may be captured and processed using the optical detector using the optical detector array 156 as described above.

Figure 3:
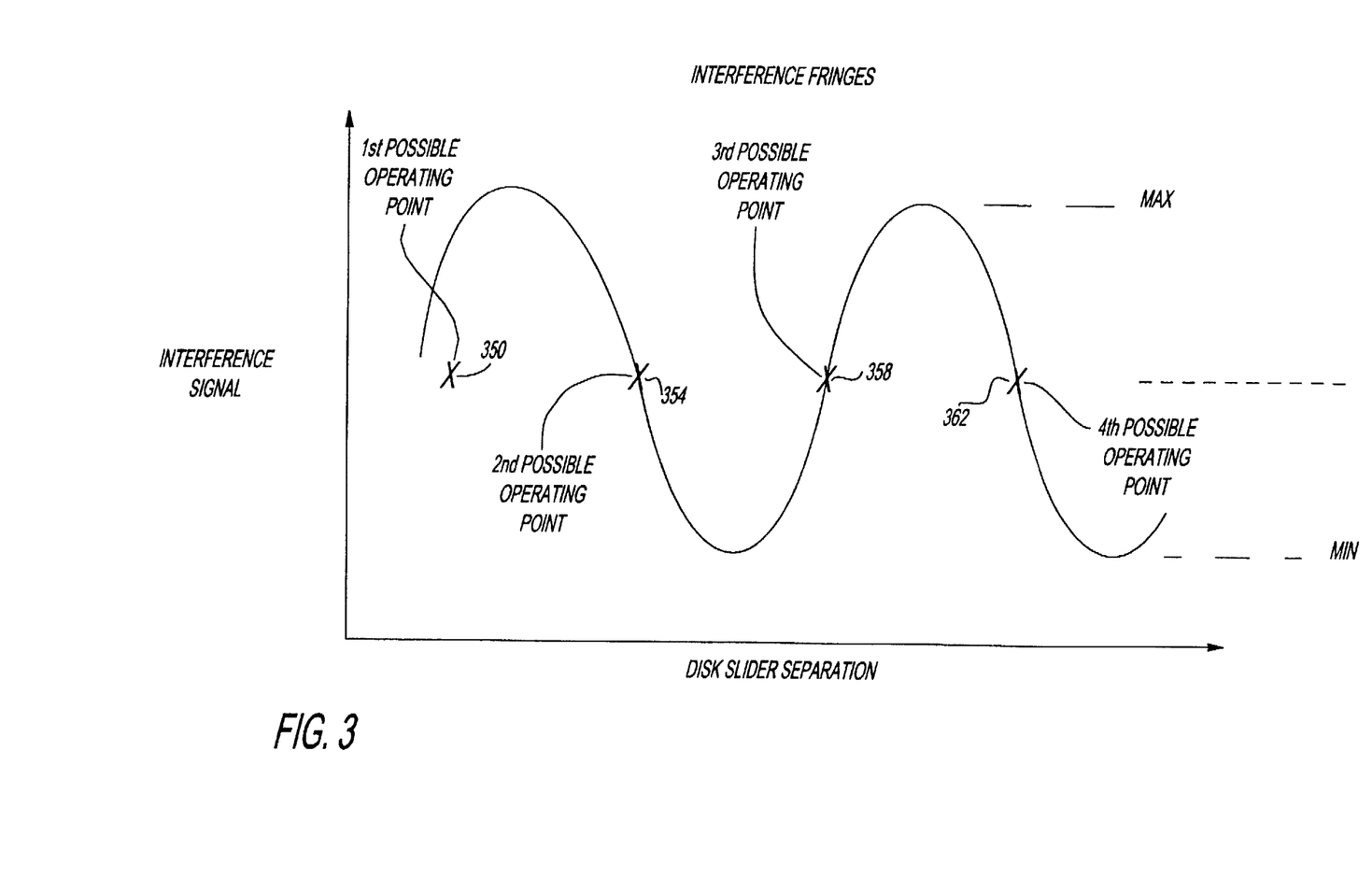
FIG. 3 is a plot of the interference signal intensity versus disk to slider spacing ("flying height"). The optimum operating point is at one of the flying heights where the slope of the curve is steepest, typically midway between a minimum and maximum of the fringe pattern.

FIG. 3 shows a plot of a typical detected interference signal as a function of disk slider separation. A typical detected fringe pattern intensity varies sinusoidally as a function of disk slider spacing as shown. In order to obtain the best sensitivity, it is preferable to operate the detection system at a point where the slope of the plot is at a maximum. Possible optimum points in FIG. 3 are 350, 354, 358 and 362. Thus the slider preferably is flown at a height such that the average disk to slider spacing corresponds to one of the identified optimum points 350, 354, 358, 362. As will be appreciated, the flying height may be adjusted by suspension loading or disk speed.

Figure 4:
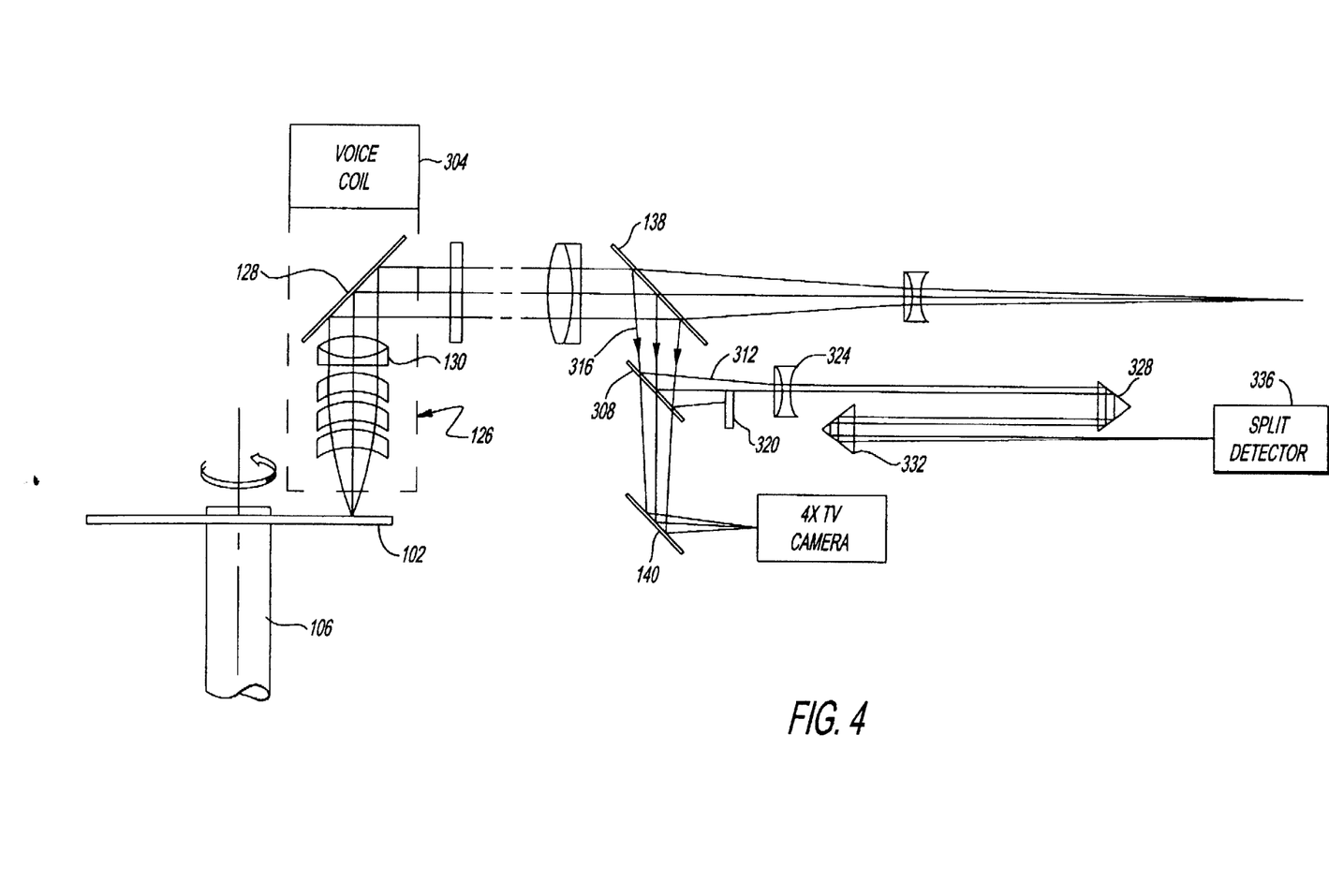
FIG. 4 is an overall view of the optical path of light through one embodiment of the optical glide tester with an emphasis on the focusing mechanism in the optical glide tester.

FIG. 4 shows a preferred embodiment of an auto focus system. Typically the objective lens 130 has a large numerical aperture, thus the depth of focus is rather shallow. In one embodiment, the depth of field of a typical microscope objective is approximately 3 micrometers. Because the test disk 102 is not perfectly flat, and the spindle bearings are not perfect, movements away from focus occur a few times during each revolution. The expected runout in a production disk may exceed the 3 micrometer depth of field by approximately a factor of 100. Thus "potato chip" disks must be compensated for by an auto focusing mechanism coupled to a voice coil 304 which moves the optical head assembly 126 or an element thereof such as lens 130 along a direction perpendicular to the disk 102 surface to keep the objective lens focused. Because the disk rotates at several thousand rotations per minute ("RPM"), the frequency response of the focusing and head gimbal positioning system must extend to several kilohertz.

A signal to adjust the auto focus mechanism may be obtained from light reflected from test disk 102. There are several techniques for deriving the focus error signal, one of these systems is depicted in FIG. 3. Light reflected from the test disk 102 reflects from reflector 128 and is split by beam splitter 138. A portion of the light reflected from beam splitter 138 reaches a second reflector 140 where light is reflected to a TV or CCD device 142. A second beam splitter 308 is inserted in the optical beam path 316 between the beam splitter 138 and reflector 140. The second beam splitter 308 creates the tertiary focusing beam 312 from the secondary beam 316. A knife edge 320 or other appropriate obscuration mechanism is used to block half of the focus beam 312. The remaining half of the focusing beam passes through lens 324 where it is focused. Secondary optical instruments such as prisms 328 and 332 may be used to further guide the beam to a detector 336.

One method of determining whether the objective is in focus is by making the detector 336 a split detector. When the disk 102 is in focus, the focus beam 312 is collimated and the secondary focusing lens 324 will focus the beam at the center of the split detector giving a difference signal $\Delta s = 0$. If the disk moves away from the objective, the focusing beam will become converging sending all the light to a first portion or half of the split detector 336. In this case, $\Delta s$ becomes positive. The amplified error signal is used to drive the auto-focus voice coil and the focusing lens element is pushed towards the disk 102. On the other hand, if the disk 102 moves too close to the lens 130, the focusing beam 312 becomes diverging and split detector 336 outputs a negative $\Delta s$ that causes the focusing lens to pull back from the test disk 102 to return $\Delta s$ to zero. It is not necessary to move the whole mass of the objective lens assembly. The preferred embodiment moves only the lens element closest to the disk, thus minimizing the moving mass and consequent vibration and contamination of the height measurements. One of ordinary skill in the art will recognize that other auto focusing schemes may also be implemented.

Figure 5:
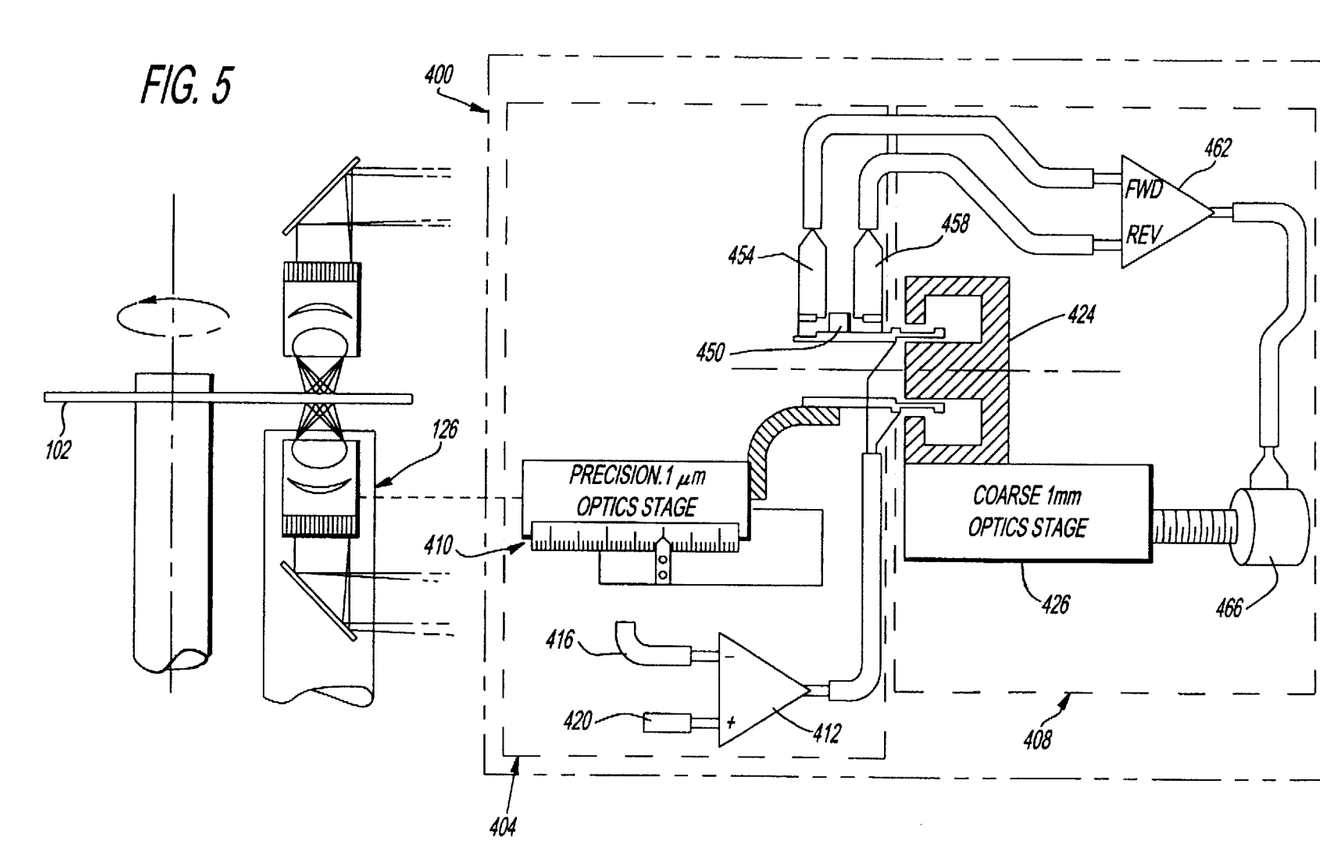
FIG. 5 illustrates one embodiment of the drive mechanism used to move and position the optical head assembly.

FIG. 5 is a diagram of a two stage radial positioning apparatus 400 which controls movement of the head gimbal assembly 126. The two stage radial positioning apparatus is comprised of a precision stage 404 and a coarse stage 408. Small precise movements are controlled by the precision stage 404 while larger movements across large sections of the disk 102 are handled by the coarse stage 408.

The precision stage 404 includes a precision optics stage 410 which measures the exact position of the head gimbal assembly 126 over the test disk 102. Information from the precision optics stage 404 is fed into an op amp or differential comparator 412 which receives input from the precision optics stage on line 416. This information is compared with the required position information input on line 420 and a linear motor 424 adjusts the movement of the precision optics stage 410 to meet the fine tuning requirements of the head gimbal assembly 126.

The linear motor 424 is coupled to the coarse optics stage 426 of the radial positioning system 400. As linear motor 424 moves the precision optics stage 410 up to the limits of the linear motor 424 movement, a contact 450 strikes sensors 454 or 458. Depending on which sensor is signaled, a controller 462 signals a motor 466 to move the entire coarse optical stage 426 accordingly. The DC motor 466 moves the head gimbal assembly 126 along a radial direction perpendicular to the rotation of the disk 102.

In an alternate embodiment, particularly in smaller disk implementations which require head gimbal assembly movement over a shorter range of distances, commercial radial positioners including single stage positioners, may be used. Such radial positioners may be purchased from Newport Corporation, 1791 Deere Avenue, Irvine, Calif., or may be constructed using precision slides and linear motors (i.e. long voice coils).

Figure 6:
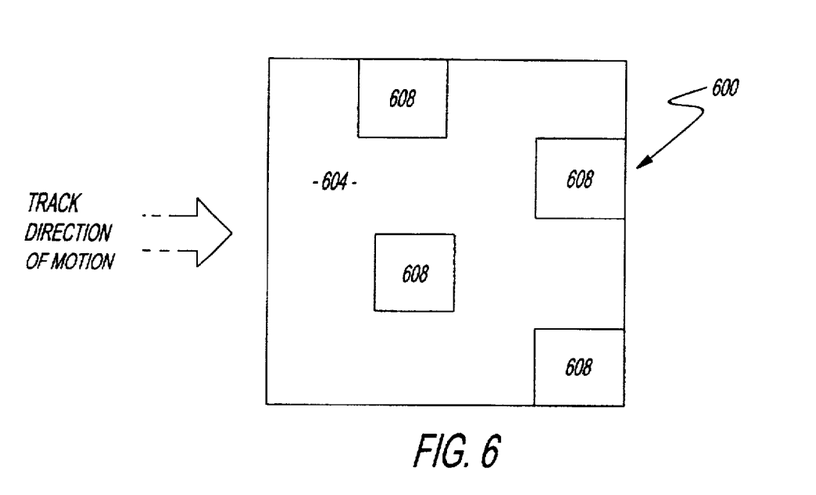
FIG. 6 illustrates one arrangement of photodiodes in a sensor array for use with the optical glide tester.

The preferred embodiment of photo-diode array 600 is shown in FIG. 6. The photo-diode array is custom designed because insulating space 604 is required between the silicon diodes 608. A single column of diodes would result in missed disk area for each scan. Hence multiple offset columns are used. Shift registers are used to contain data scanned by the first column for the time it takes for that radius of the disk to rotate under the second column. Then the data from both columns is correctly synchronized as though it had been scanned from a single contiguous line of diodes. The technique is extended to additional columns as required. The described arrangement is one embodiment which accommodates the need for having a physical insulating region between pixels yet allows exactly contiguous tracks to be scanned in a swath without missing defects which might occur in insulating regions between pixels.

Output from the photodetectors is amplified and fed to a series of feature detectors 158. The shift registers which synchronize the pixels to form a radial swath may be placed either at the output of the photodetectors or at the input of the feature detectors.

The feature detectors 158 determine which features are important and must thus be mapped. Processors significantly faster than available in current PC's would be required to handle the raw pixel data. Highly parallel pre-processing to reduce the data rate by a few orders of magnitude before input to the PC is desirable. In order to give a general idea of the processing speeds required, a discussion of a typical data transfer rate and sampling rates will follow.

A typical test disk 102 has an area of approximately 95 mm or 7,088 mm$^2$. In one embodiment, each pixel in the detector covers approximately 1.25 micrometers$^2$. The disks must be over sampled by a rate of 4× for signal processing reasons (as done in audio CDs), thus the disk will rotate one quarter of a pixel from one sample to the next. Thus the total number of samples that must be processed per disk is the over sampling rate times the number of pixels or $18.15 \times 10^9$ in the described embodiment. By dividing the data over 16 (sixteen) parallel channels, the sampling rate of each channel is reduced to a sampling rate of 37.9 MHz per channel. Thus a typical feature detector will be designed to handle a sampling rate of approximately 40 MHz or 80 Mbytes/sec data rate. For all 32 channels, this is an aggregate data rate of over 2.5 billion bytes/sec. A reasonable maximum for a input to a PC is 2.5 Mbytes/sec—1,000 times slower. Even so, the PC must handle 75 Mbytes of data in 30 seconds and this will required use of fast PCI and SCSI interfaces.

The feature detectors 158 act as filters to preliminarily determine which data is significant enough to send to the PC. The feature detectors are primarily signal processors that identify the presence or absence of a defect. In one embodiment, the feature detector acts as a window comparator, comparing data indicating "h", (height of slider from the disk at a particular time t) with an average ("Avg"). Avg is an average of slider to disk spacing measurements accumulated over a short period of time immediately preceding particular time t, say the most recent 256 pixels not including features. When a comparison, often a computed difference of h–Avg, produces a value greater than a particular threshold value, a feature vector is logged to computer 150 indicating a defect exists and that the computer should process the accompanying data. The computer 150 may then compute the height of the defect using data forwarded by the feature detector. Angle information from the radial and angular control electronics are latched at the moment of asserting a feature, and included in the feature vector so the PC can map the defects on a disk.

A typical parameter for a feature detector would be to coarsely group feature height into a few histogram categories both above and below normal. All heights either above or below normal constitute features, and are included in the feature vector to be logged into the PC. (Typically pits below −0.8 or peaks above +0.8 microinches might be minor defects, and above or below 1.2 microinches might be major defects. A disk might be acceptable with less than 1,000 minor defects and not more than 20 major defects.) However it is recognized that one of ordinary skill in the art may use other criteria than a straight threshold method to detect the presence of asperities. One such alternative involves computing the rate of variation in distance from the slider to the disk (a derivative computation). A sharp increase or decrease in slider to disk spacing indicates the presence of a defect. Such slope-based methods use differences between pixels, and so have the drawback of being noisier than summations of individual pixels.

At the computer 150, the information collected from the positioning data and from the feature detectors is coordinated. In a typical disk, the disk 102 is divided into 512 individual sectors which are synchronized to the spindle 106 rotation. Within each sector of the disk, the surface is continually scanned and the highest or lowest individual peak or pit on the disk surface is recorded as a defect for that sector.

The computer 150 measures defect height utilizing equations (1) and (2). Data is continuously streamed into the computer at high speed. The computer 150 necessarily relies on the feature flags inserted by the feature detectors for high/low minor/major defects to grade the disk. Only in off-line mode (e.g. for research or detailed quality inspection) is there time for actual height profiling or calculations in the PC. Data from feature detectors may be stored allowing for multiple grading schemes at a later time, though the data base quickly becomes voluminous. Using the stored data, "a hit map" of a disk surface may be generated. Hit maps illustrate the type and location of defects on a disk. The PC 150 then outputs the data for the end user to determine whether the disk was acceptable, to be rejected, or to be further processed. In high speed mode, the computer directly signals the robot handler to place the tested disk in the good or bad receiving trays.

The present invention described herein may be designed in many different methods and using many different configurations and parameters. While the present invention has been described in terms of various embodiments, other embodiments may come to mind to those skilled in the art with departing from the spirit and scope of the present invention. The invention should therefore be measured in terms of the claims which follow.

Optical Glide is presently a registered trademark of Thot Technologies.

What is claimed is:

1. A disk inspection apparatus for measuring surface defects comprising:

a spindle which rotates a disk;

an interferometer system which reflects an information beam from a surface of the disk and a reference beam from a reference surface;

a detector to generate a digital signal from an interference pattern formed by combing the reference beam and the information beam;

a feature detector to process an output of the detector and select features for mapping, and a processor to map features selected by the feature detector wherein said feature detector acts as a window comparator comparing a height of a slider from the disk with an average height at a particular time.

2. The disk inspection apparatus of claim 1 wherein the reference surface is a slider surface.

3. A glide tester which optically measures an asperity of a disk, comprising:

a transparent slider that is separated from the disk by an air bearing which has a height;

a light source generating a beam of light, a first portion of said beam of light is reflected from a surface of said transparent slider as a reference beam and a second portion of said beam of light is reflected from a surface of said disk as an information beam;

a detector which receives said reference beam and said information beam and converts the information beam into an electrical signal;

a feature detector which receives the electrical signal output by the detector and selects asperities which meet predetermined criteria;

a radial and angular control circuit that determines positions on a disk corresponding to asperities selected by the feature detector; and a processor that maps asperities on the disk based on the output of the feature detector and the radial and angular control electronics wherein said feature detector acts as a window comparator comparing height of slider from the disk with an average height at a particular time.

4. The glide tester as recited in claim 3, wherein said detector is a light detecting photodiode array.

5. The glide tester as recited in claim 4 wherein said photodetector array includes at least two staggered vertical columns of individual photodiode sensors, each vertical column staggered such that when the sensors are shifted in a direction perpendicular to the orientation of said vertical columns, a single row of contiguous diodes is generated.

6. The glide tester as recited in claim 5 wherein a shift register stores an output from a leading column of said two staggered vertical columns of photodiode sensors.

7. The glide tester as recited in claim 5 wherein the photodiode array scans the disk in a linear fashion by adjusting a disk rotation to be inversely proportional to a position of said slider from a center of the spinning disk.

8. The glide tester as recited in claim 3 wherein a top surface of said transparent slider includes an anti-reflection coating.

9. The glide tester as recited in claim 3 further comprising a precision optics stage to radially position the slider such that a radial position of the slider corresponds with a disk rotation such that the linear velocity of the disk under the slider is a constant.

10. The glide tester as recited in claim 3 wherein said slider is biased to fly at an optimal operating point.

11. A method for measuring the height of an asperity on a rotating disk, comprising the steps of:

generating a beam from a light source and dividing said beam into a first beam and a second beam where the first beam of light is reflected off a reference surface and the second beam of light is reflected off a surface of a rotating disk;

recombining said first beam and said second beam;

detecting an interference pattern resulting from interference between said first beam and said second beam;

identifying asperities on the disk which meet predetermined criteria using a plurality of feature detectors; and transmitting an output of the feature detectors to a processor with corresponding position information wherein said feature detectors act as a window comparator comparing a height of a slider from the disk with an average height at a particular time.

12. The method of claim 11 further comprising the step of:

computing a plurality of distances from said surface of said slider to each point in a plurality of points on the rotating disk and generating a plurality of asperity heights, each asperity height in said plurality of asperity heights corresponding to a point in said plurality of points.

13. The method of claim 11 wherein said reference surface is a surface of a transparent slider.

14. The method of claim 11 wherein said generating of said asperity heights includes the step of comparing a distance in said plurality of distances to an average height computed from said plurality of distances.

15. The method of claim 14 wherein each of said asperity heights is associated with a coordinate on said disk.

16. The method of claim 15, wherein said coordinate includes an angular position and a radial distance.

17. The method of claim 14 wherein said comparison is executed by feature detectors operating in parallel.

18. The method of claim 11 wherein said rotating of said disk is varied between a speed of 1,000 rotations per minute and 15,000 rotations per minute.

19. The method of claim 18 wherein said disk speed is adjusted to maintain an approximately constant velocity of said disk under a slider.

20. The method of claim 18 wherein said disk speed is adjusted to adjust slider to disk spacing such that the detector system operates at an optimum bias point.

21. The method of claim 11 wherein said feature detectors are set to select and forward data for asperities exceeding a predetermined height.

22. An optical measuring system which optically measures a defect of a disk comprising:
   a transparent slider that is separated from the disk by an air bearing;
   an interferometer that measures the distance from a surface of the slider to an asperity on said disk by directing a light beam such that a first beam reflects off a first plurality of first points on said transparent slider and a second beam reflects off a second plurality of second points on said disk;
   processing electronics processing the output of a detector of said interferometer to determine the distance of selected second points on said disk to corresponding first points on a surface of said transparent slider; and
   a feature detector array, at least two feature detectors in said feature detector array operating simultaneously to filter data before forwarding the data to a processor wherein said feature detector array acts as a window comparator comparing a height of slider from the disk with an average height at a particular time.

23. The optical measuring system as recited in claim 22 wherein the processor maps the asperity on said disk.

24. The optical measuring system as recited in claim 22 further comprising a feature detector array, at least two feature detectors in said feature detector array operating simultaneously to filter data before forwarding the data to a personal computer.

25. The optical measuring system as recited in claim 22 further comprising a detector array, said detector array comprising:
   a first column including a first plurality of first detectors, each first detector in said first plurality of first detectors separated from each other by a first set of insulating pixels;
   a second insulating column adjacent to said first column;
   a third column including a second plurality of second detectors wherein each second detector of said second plurality of second detectors are separated from each other by a second set of insulating pixels, said second plurality of second detectors positioned such that when said second column is shifted in a horizontal direction to overlap said first column, said second plurality of second detectors will cover said first set of insulating pixels and said second set of insulating pixels will cover said first set of first detectors.

26. The detector array of claim 25 wherein an output of said first plurality of first detectors is stored in a shift register.

27. A glide tester for detecting surface defects on a disk comprising:
   a spindle for rotating a disk;
   a transparent slider flying over a disk surface;
   an interferometer reflecting a reference beam from a surface of said transparent slider and an information beam from a surface of the rotating disk;
   a detector array detecting an interference pattern generated by the combination of the information beam and the reference beam;
   a plurality of feature detectors receiving the output of said detector array, said plurality of feature detectors generates defect information and removes excess information; and
   a processing unit which receives the defect information and characterizes the defect wherein said feature detectors act as a window comparator comparing a height of a slider from the disk with an average height at a particular time.

28. The glider tester of claim 27 in which the feature detectors processes the output of the detector by comparing a distance from the glider to a disk at a particular time with an average slider to disk spacing to generate a deviation and when the deviation exceeds a threshold, forwarding the deviation to the processor.

29. The glide tester of claim 28 wherein the feature detectors process data in real time.

* * * * *